United States Patent [19]

Yuki et al.

[11] Patent Number: 4,846,968
[45] Date of Patent: Jul. 11, 1989

[54] RESOLVING AGENT

[75] Inventors: Yoichi Yuki; Ichiro Okamoto; Tohru Shibata; Hiroyuki Nakamura, all of Himeji, Japan

[73] Assignee: Daicel Chemical Industries, Ltd., Sakai, Japan

[21] Appl. No.: 213,634

[22] Filed: Jun. 30, 1988

Related U.S. Application Data

[60] Division of Ser. No. 118,201, Nov. 6, 1987, Pat. No. 4,786,416, which is a continuation-in-part of Ser. No. 917,877, Oct. 10, 1986, abandoned, which is a continuation of Ser. No. 585,799, Mar. 2, 1984, abandoned.

[30] Foreign Application Priority Data

Mar. 10, 1983 [JP] Japan .................................. 57-39555

[51] Int. Cl.[4] .............................................. B01D 15/08
[52] U.S. Cl. ................................ 210/198.2; 210/502.1; 502/404
[58] Field of Search ...................... 55/67, 386; 210/635, 210/656, 657, 658, 659, 198.2, 198.3, 502.1; 502/62, 401, 404

[56] References Cited

U.S. PATENT DOCUMENTS

| | | | |
|---|---|---|---|
| 3,179,587 | 4/1965 | Battista | 210/198.2 |
| 3,562,289 | 2/1971 | Battista | 210/656 |
| 4,111,838 | 9/1978 | Schaeffer | 502/404 |
| 4,312,980 | 1/1982 | Motozato | 502/404 |
| 4,330,440 | 5/1982 | Ayers | 525/375 |

OTHER PUBLICATIONS

PTO Translation of "Mokuzai Kagaku," vol. 1, pp. 188–190 (1968).
Chem. Abstracts, vol. 85:122713k (1976).
Chem. Abstracts, vol. 93, No. 210783(d) (1980).
Chem. Abstracts, vol. 100, No. 16959p (1984).
Hesse, "Chromatographic Resolution of Racemates" Liebigs Ann. Chem. 1976, pp. 996–1008.
Hesse, "Complete Separation of a Racemic Mixture by Elution Chromatography on Cellulose Triacetate," Chromatographic 6(6), pp. 277–280 (1973).
"Mokuzai Kagaku.", vol. 1, pp. 188–190, title page and reverse side thereof (1968).
"Textile Research Journal", vol. XXVII, No. 4, pp. 275–287, Factors Influencing the Crystal Structure of Cellulose Triacetate, Apr. 1958.
Chemical Abstracts, vol. 97, No. 151285(a) 1982.
Enyde, "Chromatograhic Resolution of Racemic Organotin and Germanium Compounds," Journal of Organometallic Chemistry, 198 (1980), pp. 55–57.
Blaschke, "Chromatographic Separations of Racemates" XI Comparisons of Optically Active Polyamides and Cellulose Triacetate, Chem. Ber. 116, 3611–3617, Feb. 22, 1983.
Eynde, "Complete Separation of Enantiomers of a Tetraorganotin by Chromatography in Microcrystalline Cellulose Triaacetate and Fractional Crystallization", Polyhedron, 1982 1(1).

Primary Examiner—Ernest G. Therkorn
Attorney, Agent, or Firm—Flynn, Thiel, Boutell & Tanis

[57] ABSTRACT

Disclosed is an agent for resolving a mixture of optical isomers which includes cellulose triacetate of the type II form combined with a carrier as a resolving agent, to separate said isomers from each other and means for performing chromatographic elution.

11 Claims, 4 Drawing Sheets

RESOLVING AGENT

This is a division of application Ser. No. 118,201, filed Nov. 6, 1987, now U.S. Pat. No. 4,786,416, which in turn is a continuation-in-part of application Ser. No. 917,877, filed Oct. 10, 1986, now abandoned, which in turn is a continuation of application Ser. No. 585,799, filed Mar. 2, 1984, and now abandoned.

This invention relates to an optical resolving agent containing cellulose acetate of the II type and provides an optical resolving agent which exhibits an excellent power of resolving various isomers, in particular, optical isomers which have been difficult to resolve. The cellulose triacetate of type II used in the invention can be either relatively highly crystalline or relatively noncrystalline (amorphous).

There are numerous optical isomers of physiologically active compounds in the fields of pharmaceuticals, agricultural chemicals, foods, etc. Recently, optical resultion of racemic mixtures, which have heretofore been used as such, has become increasingly necessary in order to minimize damage from chemicals or to increase the effectiveness of a material, per dose. Optically active compounds having physiological activities, starting materials thereof, intermediates, catalysts for asymmetric synthesis or the like, can be readily obtained by optical resolution using the resolving agent of the present invention.

There have been few practical optical resolving agents. Optically active polytriphenylmethyl methacrylate (cf. Japanese Patent Laid-open No. 150432/1982) and optically active polymethacrylamide (cf. Japanese Pat. Laid-open No. 81891/1976) are the only synthetic high-molecular-weight materials which have been known for use as optical resolving agents. Optical resolving agents derived from natural products, such as starch (cf. West German Pat. Nos. 1013655, 1013657 and 1016713), cellulose, wool or the like have been reported. However, optical resolving agents derived from natural products have practical disadvantages, such as very low efficiency or limited fields of application.

Cellulose acetate, which is a derivative of natural cellulose, was regarded as exhibiting little optical resolving power (cf. A. Luttringhaus, V. Hess, H. J. Rosenbaum: Z. Naturforsch., B22, 1296 (1967)). However, G. Hesse et al have recently found that microcrystalline cellulose acetate, prepared by suspending microcrystalline cellullose in benzene and acetylating it in a heterogeneous system, exhibits an excellent resolving power (cf. G. Hesse, R. Hagel: Chromatographia, 6, 277 (1973); G. Hesse, R. Hagel: ibid., 9, 62 (1976); G. Hesse, R. Hagel: Liebigs Ann. Chem., 1976, 996). It has also been found that the original cellulose crystal structure still remains in the cellullose acetate, corresponding to cellulose triacetate type I.

However, because the above-mentioned microcrystalline cellulose acetate was prepared by a heterogeneous batch reaction as described above, the variations from lot to lot made it difficult to obtain optical resolving agents having consistent uniform resolving powers.

As the result of our research, undertaken to overcome the disadvantages of the microcrystalline cellulose acetate, we have discovered that crystalline cellulose acetate, the major crystal moiety of which has a crystal form of cellulose triacetate type II, is an optical resolving agent that demonstrates an excellent optical resolving power.

Thus, this invention relates to an optical resolving agent which contains crystalline cellulose acetate, the major crystal moiety of which has a crystal form of cellulose triacetate type II having a crystallization degree of at least 25%, as an active component.

Furthermore, the optical resolving agent of the invention also includes within the scope thereof cellulose triacetate of the type II having a crystallization degree of lower than 25%.

The optical resolving agent of the present invention contains cellulose triacetate type II as the major component. Cellulose triacetate type II is prepared by causing the cellulose to pass through at least one homogeneous state, that is, be dissolved, during the acetylation process of transforming cellulose into cellulose triacetate. After that, the resulting cellulose triacetate type II can be treated, if desired, to increase its crystallization degree.

Conventional resolving agents, such as cellulose acetate, are obtained by acetylating so-called microcrystalline cellulose in a heterogeneous system. Therefore, such agents are substantially cellulose acetate I. Such agents have the defect that it takes too long to elute them during the resolution step. On the other hand, we have discovered that cellulose triacetate type II, which has been dissolved once as discussed above, exhibits an optical resolving power when it is treated by an appropriate crystallization treatment. This will be a great advantage because it will make available, as a starting material, cellulose triacetate type II which is produced on a large scale in a homogeneous system. In addition, such an optical resolving agent can be processed into a desired form, such as spherical fine powder, fiber, membrane, or a porous material, depending on the intended usage. Known cellulose triacetate, optical resolving agents seem to have a crystal structure of cellulose triacetate type I, as determined by the process of the preparation thereof, whereas cellulose triacetate which is prepared by a process in which it passes through a dissolved state has a crystal structure of type II in general, regardless whether it was of type I or II prior to the dissolution. Even if the cellullose triacetate does not have the remarkable peak characteristic of type II in the X-ray photograph, it can obtain that X-ray peak characteristic by heat treatment. Consequently the optical resolving agent of the present invention has different resolution characteristics in comparison with conventional ones because of the difference in crystal structure.

The invention, unexpectedly in view of the prior art, shortens the period of time required for the elution step because the optical resolving agent is cellulose triacetate of the type II and it is more easily eluted.

Crystalline cellulose triacetate type II used in the invention can be prepared on the step of the crystallization of the cellulose triacetate type II having a low crystallinity. This will be described later on. The step of crystallization treatment is conducted, for example, by (1) changing the ratio of the swelling agent to the nonswelling agent, (2) precipitating again, etc.

It is confirmed that the conversion of cellulose triacetate type I to cellulose triacetate type II can be effected by placing it in a homogeneous state during or after the acetylation step.

As state above, the invention als is directed to the use of cellulose acetate type II having a low crystallinity, that is, having a crystallization degree of not higher than 25%. This is prepared by acetylating cellulose of the type II by either the homogeneous method or the heterogeneous method. Otherwise, it can also be obtained by acetylating cellulose of the type I by the homogeneous method or acetylating it by the heterogeneous method and then dissolving the resultant product in a solvent. Unless the product is subjected to the crystallization treatment such as mentioned before, it would usually have a low crystallinity, lower than 25%.

The term "swelling agent" refers to a solvent in which cellulose triacetate swells readily, while the term "non-swelling agent" referes to a polar solvent in which cellulose triacetate does not swell (e.g. ethanol, methanol, formamide, or water). A mixture of acetone and water (volume ratio of 8:2) and a mixture of tetrahydrofuran and water (volume ratio of 8:2) are preferred swelling agents.

The method (1) described above can be carried out by immersing cellulose triacetate in a swelling agent and adding a non-swelling agent gradually to the reaction system in order to increase the proportion of the non-swelling agent in the reaction system to thereby crystallize the cellulose triacetate, or by immersing cellulose triacetate in a mixture of swelling and non-swelling agents and distilling off the swelling agent thereby to increase the proportion of the non-swelling agent and crystallize the cellulose triacetate. The two methods can be combined. In the latter method, it is necessary to select a swelling agent having a lower vapor pressure than that of the non-swelling agent. Crystalline cellulose triacetate can be separated from the non-swelling agent by filtration or distillation. The resulting crystalline cellulose triacetate can be subjected to a heat treatment to further enhance the degree of crystallinity.

The method (2) described above can be carried out by dissolving cellulose triacetate in a solvent, such as acetone, tetrahydrofuran, chloroform, dichloromethane, methyl acetate and dimethylsulfoxide, and then gradually adding a polar precipitant, such as methanol, ethanol, formamide, or water, to increase the proportion of the precipitant thereby to crystallize the cellulose triacetate, or by dissolving cellulose triacetate in a mixture of a solvent and a precipitant and distilling off the solvent to increase the proportion of the precipitant to thereby crystallize the cellulose triacetate. The two methods can be combined. In the latter method, it is necessary to select a solvent having a lower vapor pressure than that of the precipitant. Crystalline cellulose triacetate can be separated from the precipitant by filtration or distillation. The resulting crystalline cellulose triacetate can be subjected to a heat treatment to enhance the degree of crystallinity.

The definition of cellulose and cellulose triacetate of type I and type II in the present invention will be found in, for example, "Mokuzai Kagaku" (Uda, Yonezawa and Kondo (Ed.), Kyoritsu Shuppan Co., Ltd., vol. 1, pp. 188-189), the entire contents of which are incorporated herein by reference.

The crystal form type II of crystalline cellulose triacetate in the present invention refers to one which has been called crystal form type II in the scientific literature. It is identified by the features that it exhibits three peaks in the vicinity of angles of diffraction ($2\theta$) of 8.4°, 10.4° and 13.2° in X-ray diffraction crystallography.

Cellulose triacetate type II of relatively low crystallinity is also included in the present invention. Even if cellulose triacetate has no remarkable peaks in the X-ray diffraction analysis, it can be converted by thermal treatment to one having the characteristic peaks of type II. This applies to cellulose triacetate which is dissolved, that is, is passed through the form of a solution thereof at some time during the process of obtaining the final cellulose triacetate product from the starting natural cellulose, namely, cellulose of the type I, which can be a starting material for preparing all cellulose derivatives. Cellulose triacetate I, in general, shows a slight peak in the X-ray diffraction analysis as cellulose triacetate I, for instance a single peak of $2\theta = 7.5°$ below $2\theta = 15°$, which is based on a partial crystalline area, even though it has only a low crystallization degree. Accordingly, it is distinctly different from the cellulose triacetate of type II employed in the invention. If that distinction is not found clearly, the low crystalline cellulose triacetate can be identified with thermal treatment.

The degree of polymerization of the cellulose triacetate type II used in the invention can have any value within a range of from 2 to 3000, although it is preferably from 5 to 300. The content of the free hydroxyl groups of the cellulose triacetate type II is preferably 3.2 wt. % or below, more preferably, not higher than 2.0 wt. %, most preferably, not higher than 1.2 wt. %.

The cellulose triacetate type II employed in the present inventinon can be used as an optical resolving agent as such, or by applying it onto a substrate or forming it into a membrane. Cellulose triacetate type II having a particle size of 0.01 μm to 1 cm, preferably 0.1 μm to 100 μm, can be used as an optical resolving agent for chromatography. A particle size of less than 0.01 micronmeter lowers the mechanical strength, while a particle size of larger than 1 cm lowers the efficiency of the optical resoltuion. Cellulose triacetate type II can be ground and classified mechanically by using a glass mortar, ball mill etc., or by dispersing it in a liquid in which it is insoluble and subjecting it to an ultrasonic treatment. Classification can be carried out on a filter or in a liquid utilizing the principle of differential velocity of sedimentation. Porous cellulose triacetate type II is preferable for the purposes of the invention.

Cellulose triacetate type II can be applied on a substrate by mechanical coating, chemical binding, or the like. For example, cellulose triacetate type II can be dissolved in a solvent and coated on a substrate followed by removal of the solvent and drying to thereby coat the substrate.

A substrate having appropriate voids is preferable as a carrier. The amount of cellulose triacetate type II used to coat a substrate is generally 0.01 to 100% by weight, preferably 10 to 50% by weight, based on the weight of the substrate. The substrates that can be used in the invention include porous organic carriers and porous inorganic carriers. Polymers, such as polystyrene, polyacrylamides and polyacrylates, can be used as the porous organic sbustrate. The porous inorganic carriers include synthetic and natural materials, such as silica, alumina, magnesia, titanium oxide, glass, silicates and kaolin. Those substrates can be treated on the surface thereof in advance so that they will be compatible with cellulose triacetate type II. The surface treatment can be effected with an organic silane compound for introduction of silane bonding, or by plasma polymerization.

The optical resolving agent of the present invention can be used in a conventinonal chromatographic or batch resolution. In the chromatographic method, the resolving agent of the present invention can be used as a filler for gas and liquid chromatographic columns or as a coating for thin layer chromatography. In the batch resolution, the optical resolving agent of the present invention can be added to the solution to be separated and the mechanically separated from said solution after another solution is adsorbed. In either case, it is necessary to select a solvent which brings about an excellent optical resolving power.

The optical resolving agent of the present invention can resolve a wide variety of organic or inorganic substances which consist of a mixture of at least two components which are soluble in a common solvent. It is particularly suitable for resolving isomers which have been difficult to resolve heretofore, such as geometrical and optical isomers. In addition, it can be used in gel permeation chromatography.

Examples of geometrical isomers which can be resolved are cis- and trans-isomers and disubstituted aromatic isomers, such as o-xylene, m-xylene, and p-xylene.

A wide variety of optical isomers can be resolved by the optical resolving agent of the present invention. In particular it is effective to resolve compounds having an asymmetric carbon or nitrogen atom, such as 2-phenylcyclohexanone, 2-(1-phenylethyl)anisole, Troeger's base, N-methylbarbital derivatives, cyanoacetate, and trans-1,2,-diphenyl cyclopropane; and molecular-asymmetric compounds which are optical isomers with no asymmetric carbon atom and have been difficult to resolve.

Preferable optical isomers to be treated in the invention include compounds having asymmetric centers and compounds of molecular dissymmetry. One of the optical isomers is retained more than the other when the optical resolving agent of the invention is used.

DESCRIPTION OF THE PREFERRED EMBODIMENTS

To further illustrate this invention, but not by way of limitation, the following examples are given. The physical properties described in the following examples were determined as follows.

1. Degree of crystallinity

The degree of crystallinity was determined by X-ray diffraction crystallography with $Cu_{\alpha 1}$-radiation by using a Geigerflex (a product of Rigaku Denki Co.).

The degree of crystallinity can be determined theoretically by dividing the X-ray diffraction spectrum into two parts corresponding to crystalline scattering and non-crystalline scattering, respectively, and substituting them in the following equation.

$$\text{Degree of crystallinity (\%)} = \frac{\text{Intensity of crystalline scattering}}{\text{Intensity of crystalline scattering} + \text{Intensity of non-crystalline scattering}} \times 100$$

However, it is very difficult to carry out this division actually without making arbitrary distinctions. Therefore, the intensities of crystalline and non-crystalline scattering were determined, as approximations, by the following procedures in order to eliminate the arbitrariness. Consequently, this data cannot be directly compared with those reported in other publications.

Figure 1:
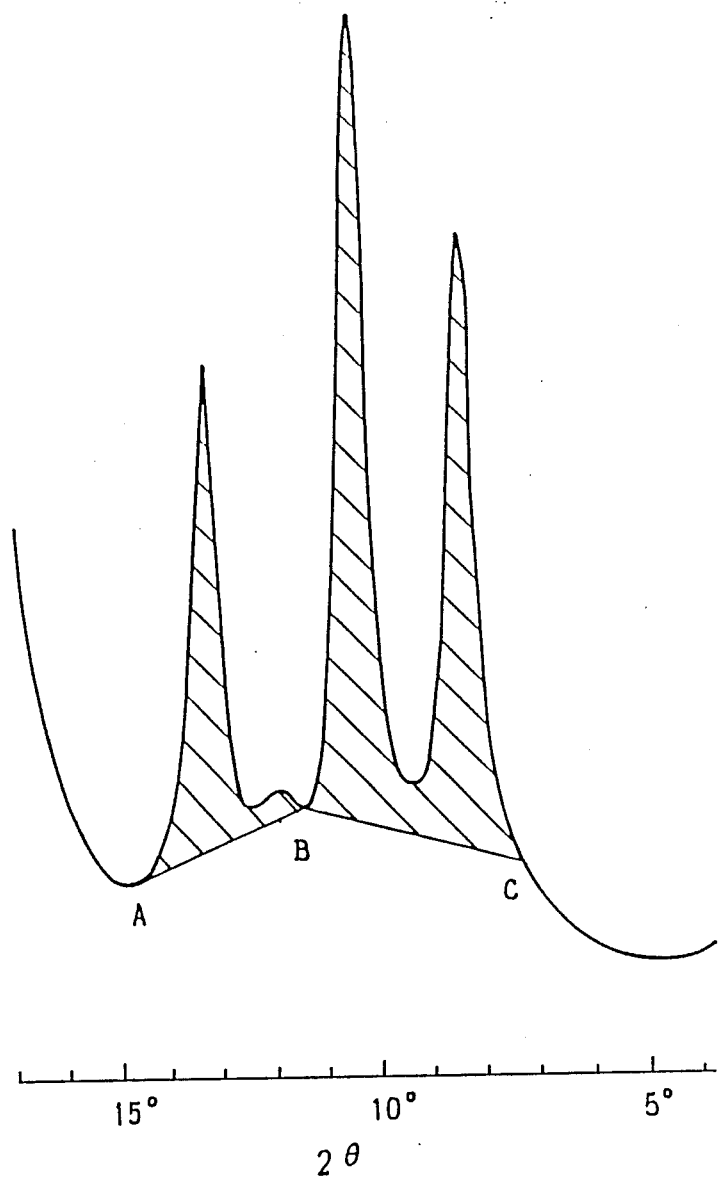
FIGS. 1 and 2 are X-ray diffraction spectra of crystalline cellulose triacetate and non-crystalline cellulose triacetate, respectively.
Figure 2:
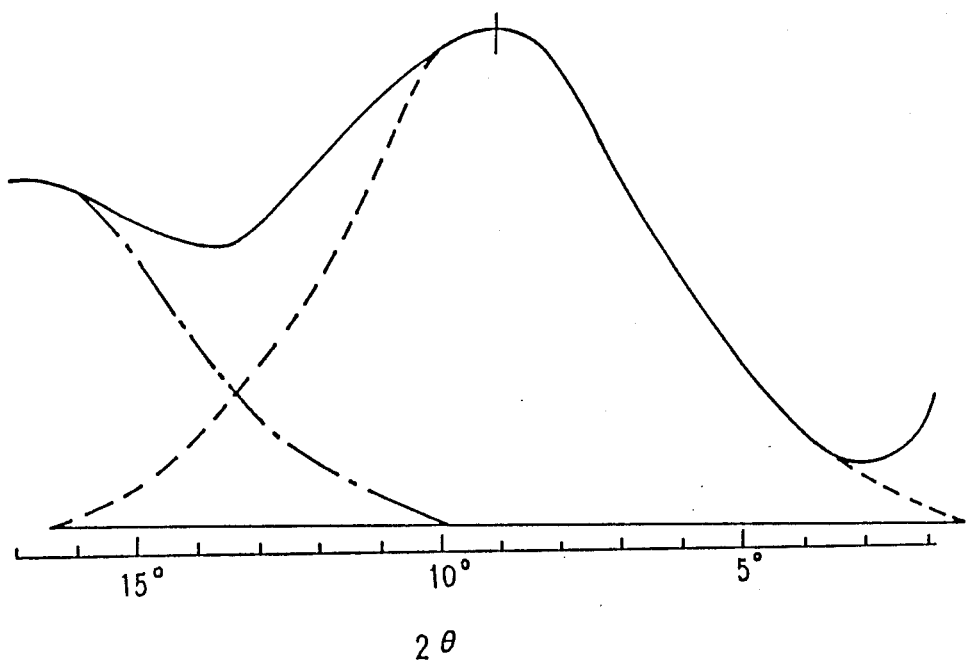

FIG. 1 shows the X-ray diffraction spectrum of a crystalline cellulose triacetate type II used in the present invention as an example. The crystalline scattering part was approximated by the upper part (shaded part in FIG. 1) of the line connecting three points A, B and C on the diffraction curve corresponding to angles of diffraction (2θ) of: 14.4° (point A); 11.4° (point B); the minimum point: spectra in which no minimum point was observed at this point were regarded as "showing a low degree of crystallinity" (in the gross); and 7.2° (point C). The non-crystalline scattering part was determined as follows. FIG. 2 shows an X-ray diffraction spectrum of a non-crystalline cellulose triacetate sample which was regarded as having the lowest degree of crystallinity. The spectrum was divided into two symmetrical curves having a peak at 2θ=9° and 2θ=17° respectively (the broken line and the dot-dash line in FIG. 2). Then the non-crystalline scattering part corresponding to the crystalline scattering part as desribed above was approximated by a curve which had the same distribution as the one having the center at 2θ=9° and the same peak intensity with the scattering intensity at point B in FIG. 1. In both spectra, the scattering intensity of 2θ=40° was extrapolated as a base line.

2. Degree of polymerization 2-1. Vapor pressure osmometry

The degree of polymerization was determined by a vapor pressure osmometer CORONA 117 with a solvent mixture of chloroform and 1% ethanol.

2-2. Viscometry

The degree of polymerization was determined by the following equation by using dichloromethane/methanol (9:1) as a solvent, approximating [η] by the reduced viscosity of a 0.2% solution and regarding $K_m$ as $5.65 \times 10^{-4}$:

$$\text{Degree of polymerization } \overline{DP} = [\eta]/K_m.$$

3. Determination of free hydroxyl group content

This determination was carried out according to a method of phenylcarbamoylation of a hydroxyl group as reported by Carl J. Malm et al (cf. Anal. Chem. 26, 188 (1954)). That is, cellulose triacetate was treated with a large excess of phenyl isocyanate in pyridine at 90° C. for 30 min, followed by purification by reprecipitation. Then the amount of phenylcarbamoyl groups formed by the reaction between the hydroxyl group and phenyl isocyanate was determined by UV absorbance at 272 nm. The molar absorptivity of the carbamoyl group was set as 705, which had been determined from cellobiose heptaacetate carbanylate. The determined data was expressed as the hydroxyl group content (% by weight) in the original cellulose triacetate.

4. Determination of particle size

Particle size distribution was determined by suspending the resulting fine cellulose acetate particles in an electrolyte (Isoton II ®) by using an aperture of 100μ and a Coulter Counter ® Model TA-II (a product of Nikkaki Hanbai Co., Ltd.).

SYNTHESIS EXAMPLE 1

140 g of commercially available cellulose triacetate (average $\overline{DP}=111$ as determined by vapor pressure osmometry; molecular weight distribution $M_w/M_n=2.45$; free hydroxyl group content=0.35 wt.

%) was allowed to swell in 1.4 l of acetic acid. Then 23.2 ml of acetic anhydride, 7.0 ml of sulfuric acid and 8.4 ml of water were added and the resulting mixture was allowed to react for three hours at 80° C. Subsequently the reaction mixture was cooled with ice water and the sulfuric acid was neutralized by adding 86.8 g of a 26% solution of magnesium acetate. The resulting solution was added to a solvent mixture of water and isopropanol (IPA) to precipitate cellulose acetate. The precipitate was filtered and dried. Cellulose acetate thus obtained was dissolved in acetone and the insoluble material was removed by pressurized filtration. Then water was added in an amount so as not to form any precipitate and the solvent was distilled off by a rotary evaporator. The resulting white powder was dried in vacuo.

The resulting porous cellulose acetate was cellulose triacetate type II having a degree of crystallinity of 46%, as determined by X-ray diffraction. The average degree of polymerization $\overline{DP}$ thereof was 23, determined by viscometry.

SYNTHESIS EXAMPLE 2

Cellulose triacetate having a number-average degree of polymerization of 110 and a hydroxyl content of 0.35 wt. % was ground with a vibratory grinder, and the powder that passed through a screen of 250 mesh was collected. In the X-ray diffraction spectrum of this powder, three peaks within the range of $2\theta = 8°$ to $14°$, indicative of crystalline cellulose triacetate type II, were not observed, thus indicating that the powder had a very low degree of crystallinity. 10 g of the powder was suspended in a mixture of 10 ml of acetone and 5 ml of water in a flask. Then 65 ml of acetone was added slowly with stirring. Subsequently a distillation apparatus was fitted with the flask and approximately 100 ml of water was added slowly while distilling off the acetone. When the boiling point of the distillate reached 90° C., the distillation was stopped and the system was allowed to cool. The cellulose triacetate powder was separated by a glass filter, washed with water and dried in vacuo at room temperature. The product was found to be cellulose triacetate type II. The degree of crystallinity of the resulting product was evaluated as 32%.

EXAMPLE 1

Cellulose acetate prepared in Synthesis Example 1 was ground by ultrasound treatment (28 kHz) in ethanol and then was classified according to its particle size depending on the differential velocity of the sedimentation thereof. The cellulose acetate having a low velocity of sedimentation was packed in a stainless steel column (0.4 cm in diameter×25 cm in length) by a slurry method. Optical resolution of racemates listed below were effected by using this column (cf. Table 1). A Tri Rotor SR (a product of Nippon Bunko Kogyo Co., Ltd.) was used as a liquid chromatography device while a Uvidec-IV (a product of Nippon Bunko Kogyo Co., Ltd.) was used as a detector. Ethanol was used as the carrier solvent at a rate of 0.2 ml/min. The dead volume of the column was 2.5 ml as measured with hexane. The results are shown in Table 1, FIG. 3 and FIG. 4. In Table 1 each term was defined as follows.

$$\text{Capacity factor } (k') = \frac{\text{Retention time of antipode} - \text{Dead time}}{\text{Dead time}}$$

$$\text{Separation factor } (\alpha) = \frac{\text{Capacity factor of antipode adsorbed more intensively}}{\text{Capacity factor of antipode adsorbed less intensively}}$$

$$\text{Resolution factor } (R_s) = \frac{\text{Distance between peaks of antipodes adsorbed more intinsively and less intensively}}{\text{Total band-width of both peaks}}$$

TABLE 1

| Racemate | capacity factor (k') | capacity factor (k') | separation factor (α) | resolution factor (Rs) |
|---|---|---|---|---|
| trans-stilbene oxide | 0.99 | 1.34 | 1.35 | 0.91 |
| Troeger's base | 0.64 | 0.97 | 1.52 | 0.80 |

Figure 3:
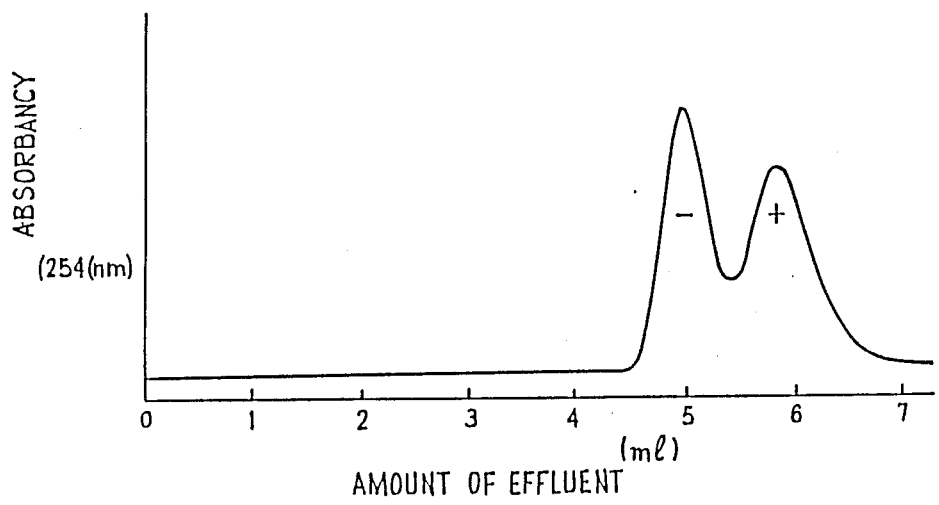
FIGS. 3, 4 and 5 are optical resolution curves obtained by using the optical resolving agent of the present invention.
Figure 4:
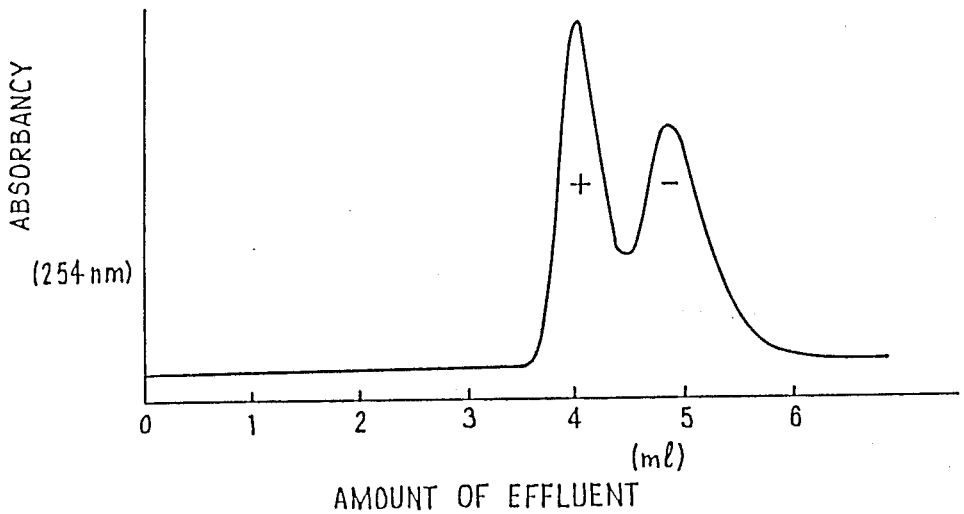

FIG. 3 shows the optical resolution of transtilbene oxide, while FIG. 4 shows that of Troeger's base, wherein + and − represent signs of the rotatory power with D-radiation.

For comparison, finely crystalline cellulose triacetate type I was synthesized according to the method by G. Hesse et al. The product was ground and a column was charged therewith. The optical resolution was conducted with ethanol as a solvent in the same manner as described above. The capacity factor for trans-stilbene oxide was 7.82 and 11.3. The capacity factor for Troeger's base was 2.61 and 5.36. It is understood from these results that the filler according to the invention had a smaller capacity factor and provides a much quicker analysis than the control.

EXAMPLE 2

Crystalline cellulose triacetate prepared in Synthesis Example 2 was packed in a column in the same manner as described in Example 1 to effect optical resolution of trans-stilbene oxide. The separation factor was 1.25.

EXAMPLE 3

20 g of commercially available cellulose triacetate type II obtained by a conventional homogeneous acetylation (the number-average degree of polymerization determined by vapor pressure osmometry $\overline{DP} = 111$; free hydroxyl group content=0.35% by weight) was dissolved in a solvent mixture of 360 ml of dichloromethane and 40 ml of methanol. The resulting solution was added to 1.2 l of water containing 3.0 g of gelatin, 1.0 g of MonogenUni (a product of Dai-ichi Kogyo Seiyaku Co., Ltd.) and 1.0 g of Antifoam E-20 (a product of Kao Soap Co., Ltd.), and stirred for 40 min by an Ultra-homomixer (3600 rpm; a product of Nippon Seiki Seisakusko Co., Ltd.) to form an emulsion. Said emulsion was introduced into a three-necked flask and maintained at 35° to 40° C. for three hours, 40° to 45° C. for three hours, and then 50° to 60° C. for an hour on a water bath with stirring. During this period, the upper space of the flask was aerated to remove the dichloromethane. The resulting suspension was allowed to stand for 15 hours and the supernatant was removed. Then it was dispersed into water to remove the supernatant by decantation and washed. Finally it was passed through a screen of 40μ to remove large masses. Thus, cellulose triacetate type II was obtained in the form of spherical fine particles having the largest particle size of 8μ in number distribution and 12μ in volume distribution. An X-ray diffraction spectrum of the resulting compound identified it as type II and it had no minimum scattering intensity in the vicinity of $2\theta = 11.4°$, suggesting that it had a low degree of crystallinity (i.e. less than 25%) according to the definition as described above.

EXAMPLE 4

Figure 5:
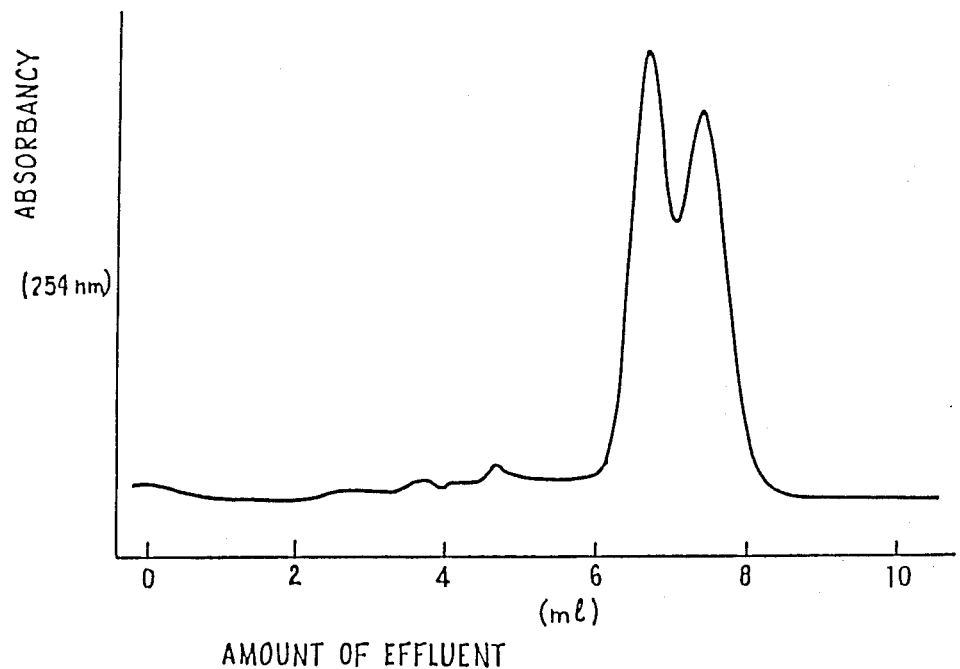

Fine particles of cellulose triacetate type II of low crystallinity prepared in Example 3, were suspended in ethanol and packed in a stainless steel column (0.4 cm in diameter×25 cm in length) by a slurry method. The optical resolution of trans-stilbene oxide was carried out by using this column. FIG. 5 shows the elution curve thus obtained. A Tri Rotor SR (a product of Nippon Bunko Kogyo Co., Ltd.) was used as a liquid chromatography device and Uvidec-100-IV manufactured by the same company was used as a detector. Ethanol was used as an eluent at an elution velocity of 0.2 ml/min, and the detection was carried out at 254 nm.

EXAMPLE 5

100 g of the same cellulose triacetate as used in Example 3 was dissolved in 500 ml of dichloromethane. Then 100 ml of 100% acetic acid was added and stirred thoroughly. The dichloromethane was distilled off by using a rectifying column to obtain an acetic acid solution of cellulose triacetate. 2 ml of acetic anhydride and 5 ml of 95% conc. sulfuric acid were added to the resulting solution maintained at 80° C. with stirring. Then the reaction mixture was allowed to react for three hours to lower the molecular weight. The reaction was stopped by neutralizing the sulfuric acid with an excess of a solution of magnesium acetate. The resulting liquor was added to water in a large excess and the formed precipitate was filtered and washed with water. After drying in vacuo, it was dissolved in dichloromethane and purified by reprecipitating it with a large excess of isopropyl alcohol, followed by drying in vacuo. This product was identified as cellulose triacetate by infrared and NMR spectra. The number-average degree of polymerization thereof was 25, as determined by vapor pressure osmometry.

This compound was treated with phenyl isocyanate in pyridine according to a method reported by Caul J. Malus et al (Anal. Chem., 26, 188 (1954)). Only trace UV absorption was observed at 272 nm, corresponding to the wavelength of phenyl carbamate which might be formed by the reaction of phenyl isocyanate and the free hydroxyl groups, if any, in the compound, suggesting that there was few free hydroxyl groups in this compound. Yield; 86 g.

It was further identified as cellulose triacetate type II by X-ray diffraction and the degree of crystallinity thereof was not more than 25% (low crystallinity).

EXAMPLE 6

10 g of silica beads, Li Chrospher SI1000, which is a trademark of a product of Merck, were introduced into a 200 ml, branched, round-bottomed flask in an oil bath. They were dried in vacuum for 3 hours at the oil bath temperature of 120° C. and then nitrogen gas was introduced into the flask. 100 ml of toluene, which had been obtained by evaporation together with $CaH_2$, was added to the silica beads. Thereafter 3 ml of diphenyldimethoxysilane, KBM202, which is a trademark of a product of Shinetsu Kagku, was added thereto and the mixture was stirred. The reaction of the mixture was conducted at 120° C. for 1 hour. After 3 to 5 ml of toluene was distilled out, the reaction was continued for a further 2 hours 120° C. The reaction product was filtered with a glass filter and washed three times with 50 ml of toluene and then three times with 50 ml of methanol. It was then dried at 40° C. for 1 hour.

About 10 ml of the thus-treated silica beads were introduced into a 200 ml, branched, round-bottomed flask and dried in vacuum at 100° C. for 3 hours. The pressure in the flask was allowed to reach normal pressure and cooled at room temperature, followed by introducing nitrogen gas thereinto. 100 ml of distilled toluene was added to the dried silica beads. One m of N,N-bis-(trimethylsilyl)acetamide as a trimethylating agent was added thereto and the mixture was stirred. The reaction was effected at 115° C. for 3 hours. The reaction product was filtered with a glass filter and washed with toluene, followed by drying in vacuum for about 4 hours.

1.6 g of cellulose triacetate obtained in Example 5 was dissolved in 10 ml of methylene chloride and the solution was filtered with G-3 glass filter. Then 3.5 g of the silica beads treated with a silane and 5.5 ml of the solution of cellulose triacetate were mixed with each other and the solvent was distilled out under a reduced pressure so that the silica beads treated with a silane might be coated with the cellulose triacetate. This was used as an optical resolving agent.

EXAMPLE 7

The filter prepared in Example 6 was packed in a stainless steel column (4.6 mm in diameter×250 mm in length) by a slurry method. Table 2 shows the results of optical resolution of various compounds achieved by using this column. The same instruments as described in Example 4 were used. Ethanol or a mixture of hexane/isopropyl alcohol (IPA) (9:1) was used as an eluent at an elution velocity of 0.2 ml/min.

TABLE 2

Optical resolution of various racemates by cellulose triacetate carried by silica gel beads

| Recemate | Solvent | capacity factor (k) | capacity factor (k) | separation factor (α) | resolution factor (R_s) |
|---|---|---|---|---|---|
| (structure: O-bridged dinaphthyl) | Ethanol | 0.57 | 0.65 | 1.14 | 0.82 |
|  | Hexane-IPA | 0.49 | 0.60 | 1.22 | 0.97 |
| (structure: N,N-diaryl bicyclic) | Ethanol | 0.49 | 0.57 | 1.15 | 0.67 |
|  | Hexane-IPA | 0.39 | 0.51 | 1.31 | 1.33 |
| (structure: benzosuberone) | Ethanol | 0.55 | — | 1 | 0 |
|  | Hexane-IPA | 0.73 | 0.78 | 1.07 | — |
| (structure: bis-CONH-phenyl) | Ethanol | 0.16 | — | 1 | 0 |
|  | Hexane-IPA | 1.19 | 1.34 | 1.13 | 0.54 |
| (structure: benzoin) | Ethanol | 0.22 | — | 1 | 0 |
|  | Hexane-IPA | 1.81 | 1.92 | 1.05 | — |
| (structure: phenyl-C(OH)-C(=O)-NH2) | Ethanol | 0.14 | — | 1 | 0 |
|  | Hexane-IPA | 3.25 | 3.52 | 1.08 | 0.67 |

We have compared the optical resolution ability between cellulose triacetate I (CTA I) and cellulose triacetate II (CTA II) and, to the best of our knowledge, have found that CTA I cannot resolve the following compounds while CTA II can.

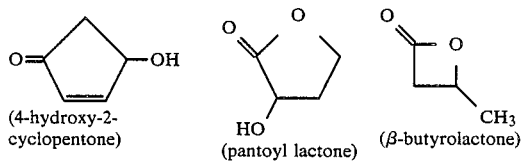

(4-hydroxy-2-cyclopentone)  (pantoyl lactone)  (β-butyrolactone)

CTA I and CTA II differ from each other in column efficiency. The sharpness and narrowness of a peak provided by a packing in a chromatographic separation column is one measure for indicating the performance of that packing. In order to obtain a packing having a high efficiency (i.e., providing a sharp peak), the packing should be in a porous, fine, spherical form. The dissolution of CTA I brings about an irreversible loss of its structure and crushing CTA I into a powder comprising particles having nonuniform shapes is the only known way to produce a finely divided powder suitable for use as a column packing. Therefore, there is a limitation to the efficiency of a column prepared using such a packing and difficulties are encountered in producing a column having a number of column plates exceeding 2000 with high reproducibility as was determined by using a column having a length of 25 cm [sample: benzene 0.1 μl; eluent: 95% ethanol; temp.: room temp.; flow rate: 0.5 ml/min; column size (inner diameter: 0.46 cm; length: 25 cm)]. However, since CTA II can be processed in a dissolved state, it is possible to produce a column having a high efficiency using the CTA II as adsorbent material. A column having the same dimensions as the above-mentioned tower was packed with a packing comprising a microporous silica gel (e.g. Lichrospher Si 1000, a product of Merck) having 20% of CTA II supported thereon to provide a number of theoretical plates as high as 3000 to 8000 as determined in the same manner as above with respect to CTA I with the exception of a hexane/2-propanol mixture (9:1) being used as the eluent.

CTA I and CTA II have differenti properties when combined with an eluent. In column chromatography, various eluents may be selected depending on the kinds of substances to be separated and the purpose of the separation. The following table shows the separation factors provided by CTA I and CTA II (supported on silica gel) with respect to different eluents.

TABLE 3

| compound eluent | O[Ph, Ph] A | CH$_3$ B | N—CH$_3$ A | N—CH$_3$ (bicyclic) B |
|---|---|---|---|---|
| α (CTA I)  | 1.0     | 1.75 (+) | 1.0      | 1.97 (−) |
| α (CTA II) | 1.22 (−)| 1.18 (−) | 1.20 (−) | 1.18 (+) |

Note:
A ... hexane/2-propanol mixture (9:1)
B ... 95% aqueous ethanol

CTA I has an excellent separation capacity when combined with an eluent composed mainly of a polar liquid such as ethanol but exhibits no separation capacity when combined with a nonpolar eluent composed mainly of hexane. CTA II exhibits a separation capacity when combined with a nonpolar eluent composed mainly of hexane as well as with an eluent composed mainly of a polar liquid. Therefore, the properties of CTA I and CTA II are different from a practical point of view.

What is claimed is:

1. An optical resolving agent which comprises cellulose triacetate consisting essentially of the type II form, combined with a solid carrier effective for use to resolve a mixture of optical isomers and means for performing chromatographic elution.

2. The optical resolving agent of claim 1, wherein said cellulose triacetate has a crystallization degree of at least 25 percent.

3. The optical resolving agent of claim 1, wherein said cellulose triacetate has a crystallization degree of lower than 25 percent.

4. The optical resolving agent of claim 1, wherein said cellulose triacetate has a degree of polymerization of from about 2 to about 3000, and the content of free hydroxyl groups is not higher than 3.2 wt. %.

5. The optical resolving agent of claim 1, wherein said cellulose triacetate has a particle size of 0.1 μm to 100 μm.

6. The optical resolving agent of claim 5, wherein saidcellulose triacetate particles are deposited on a solid porous catalyst in an amount of from 0.01–100% by weight, based on the weight of the carrier.

7. The optical resolving agent of claim 1, wherein said solid carrier is selected from the group consisting of porous organic carriers and porous inorganic carriers.

8. The optical resolving agent of claim 1, wherein said solid carrier is a porous organic carrier selected from the group consisting of polystyrene, polyacrylamides and polyacrylates.

9. The optical resolving agent of claim 1, wherein said solid carrier is a porous inorganic carrier selected from the group consisting of silica, alumina, magnesia, titanium oxide, glass, silicates and kaolin.

10. The optical resolving agent of claim 1, wherein said solid carrier is surface treated.

11. The optical resolving agent of claim 1, wherein said solid carrier is surface treated with an organic silane compound.

* * * * *